United States Patent [19]

Banks et al.

[11] Patent Number: 4,764,593

[45] Date of Patent: Aug. 16, 1988

[54] MANUFACTURE AND EXPRESSION OF GENES FOR UROGASTRONE AND POLYPEPTIDE ANALOGS THEREOF

[75] Inventors: Allen R. Banks; David L. Hare, both of Boulder, Colo.

[73] Assignee: Amgen Inc., Thousand Oaks, Calif.

[21] Appl. No.: 731,751

[22] Filed: May 7, 1985

Related U.S. Application Data

[63] Continuation of Ser. No. 486,091, Apr. 25, 1983, abandoned, which is a continuation-in-part of Ser. No. 375,500, May 6, 1982, abandoned.

[51] Int. Cl.$^4$ .............................................. C07K 7/00
[52] U.S. Cl. .................................. 530/324; 530/350; 530/399; 530/820; 530/825; 530/834; 435/68; 435/70
[58] Field of Search ............... 530/350, 324, 399, 820, 530/825, 834; 435/68, 70

[56] References Cited

U.S. PATENT DOCUMENTS

| | | | |
|---|---|---|---|
| 3,883,497 | 5/1975 | Gregory et al. | 260/112 R |
| 4,032,633 | 6/1977 | Gregory et al. | 424/177 |
| 4,035,485 | 7/1977 | Gregory et al. | 424/177 |
| 4,568,640 | 2/1986 | Rubin | 435/68 |

FOREIGN PATENT DOCUMENTS

0046039  2/1982  European Pat. Off. .............. 435/68

OTHER PUBLICATIONS

*Nucleic Acid Res.*, (10), 1982, Smith et al., Chemical Synthesis and Cloning of a Gene for Human B–Urogastrone., p. 4467.
*Science* (221), 1983, Scott et al., Structure of a Mouse Submaxillary m-RNA Encoding . . . Protein, p. 236.
*Nature* 303(5919), 1983, Gray, Nuclestide Sequence of EGF CDNA Prel . . . Precursor, p. 722.
*Cancer Res.* 41, 1981, Moses et al., Transforming Growth Factor Production by Chemically Transformed Cells.
Adamson et al., *Mol. Cell. Biochem.*, 34: 129–152 (1981).
Carpenter, *Birth Defects: Original Article Series*, 16: 61–71 (1980).
Cohen, *J. Biol. Chem.*, 237: 1555 (1962).
Fabricant et al., *PNAS (U.S.A.)*, 74: 565–569 (1977).
Frey et al., *Proc. Nat. Acad. Sci.*, 76(12): 6294–6298 (1979).
Gray et al., *Science*, 88: 489 (1939).
Gregory, *Nature (London)*, 257: 325–327 (Sep. 1975).
Hollenberg, *Vitamins & Hormones*, 37: 69–110 (1979).
Starkey et al., *Science*, 189: 800–803 (1974).

*Primary Examiner*—Morton Foelak
*Assistant Examiner*—Garnette D. Draper
*Attorney, Agent, or Firm*—Marshall, O'Toole, Gerstein, Murray & Bicknell

[57] ABSTRACT

Disclosed are DNA sequences comprising structural genes coding for (1) a polypeptide having the amino acid sequence and properties of urogastrone and for (2) polypeptide analogs thereof which differ in terms of the identity and/or location of one or more amino acids, e.g., [Asp$^{25}$] and Pro$^{52}$, Pro$^{53}$] analogs of urogastrone. Structural gene sequences may be provided with initial and terminal sequences which facilitate production of discrete protein products by selected host microorganisms as well as for expression by host organisms of fusion proteins, e.g., β-lactamase-urogastrone and β-galactosidase-urogastrone from which the desired products may be isolated.

2 Claims, No Drawings

MANUFACTURE AND EXPRESSION OF GENES FOR UROGASTRONE AND POLYPEPTIDE ANALOGS THEREOF

This application is a continuation of application Ser. No. 486,091, filed 4/25/83, now abandoned, which a continuation-in-part of prior co-pending U.S. patent application Ser. No. 375,500, filed May 6, 1982, now abandoned.

BACKGROUND

The present invention relates generally to the manipulation of genetic materials and, more particularly, to the manufacture of specific DNA sequences useful in recombinant procedures to secure the production of urogastrone and polypeptide analogs thereof.

Incorporated by reference herein for the purpose of providing information pertinent to the prior art with respect to recombinant DNA techniques is co-owned, co-pending U.S. patent application Ser. No. 375,493, filed May 6, 1982, now U.S. Pat. No. 4,652,639, by Yitzhak Stabinsky, entitled "Manufacture and Expression of Structural Genes".

A component in human urine which inhibits gastric acid secretion was first described by Gray in 1939 [Gray, et al., *Science*, 89, 489 (1939)]. This component, named "urogastrone" was completely sequenced and its structure was published in 1975 [N. Gregory, *Nature (London)*, 257, 325 (1975)]. Earlier, the isolation and characterization of a factor from mouse salivary glands which promotes the growth of epidermal tissue had been published [Cohen, *J. Biol. Chem.*, 237, 1555 (1962)]. This compound was called "epidermal growth factor". When the amino acid composition of epidermal growth factor was compared with that of urogastrone, it was found that the two peptides were closely related. It is now known that these compounds, mouse and human epidermal growth factor-urogastrone (EGF-URO), are examples of a large class of "growth factors" and are widespread in animals and man.

EGF-URO like the other growth factors such as insulin, nerve growth factor, the insulin-like growth factors, and the like, is synthesized in mammals as part of a larger "pro-peptide" molecule from which it is cleaved by specific proteases to liberate the active form of the protein [Frey, et al., *Proc. Nat. Acad. Sci.*, 76, 6294 (1979)]. When cleaved from its pro-peptide, EGF-URO, in both the mouse and in man, is composed of 53 amino acids. Further processing in the body also gives rise to a 51 amino acid-containing form which lacks the two amino acid residues at the carboxyl terminus of the peptide. The 53 and 51 amino acid forms of the peptide are called beta- and gamma- EGF-URO, respectively. Both forms have shown high activity as inhibitors of gastric acid secretion and as stimulators of growth of epidermoid tissue. High gastric secretion inhibitory activities have also been reported for the 46 and 47 amino acid products of selective enzymatic degradation. [See, U.S. Pat. Nos. 4,032,633 and 4,035,485.]

Receptors for EGF-URO have been found in various tissues of the human, mouse, rat, chicken, rabbit, cow, monkey, dog, cat, mink and hamster [Adamson, et al., *Mol. Cell. Biochem.*, 34, 129 (1981)]. Work done with mouse and human EGF-URO has shown that they have identical activities in both species, the best documented of which are the abilities to virtually stop gastric acid secretion and to cause proliferation of epidermal and other epithelial tissues. [See, e.g, Starkey, et al., *Science*, 189, pp. 800–803 (1974) and Carpenter, *Birth Defects: Original Article Series*, 16, pp. 61–72 (1980)].

Despite its significant biological activities, little has been done to explore the full clinical potential of urogastrone and synthetic analogs thereof. This is due in large part to lack of large quantities of the substance. EGF-URO is presently isolated in small quantities by purification from mouse salivary glands or by a complex purification from human urine [Hollenberg, *Vitamins and Hormones*, 37, 69 (1979); Gregory et al., U.S. Pat. No. 3,883,497].

The polypeptide substance is too large to be readily synthesized by the well-known Merrifield procedure. Recombinant DNA techniques for the manufacture, cloning and expression of a structural gene for urogastrone and genes for polypeptide analogs which differ therefrom in terms of the identity and/or location of one or more amino acids have not been brought to bear on this problem.

BRIEF SUMMARY

Provided by the present invention is a manufactured gene capable of directing synthesis in a selected host microorganism of urogastrone. In a preferred form of manufactured gene, the base sequence includes one or more codons selected from among alternative condons specifying the same amino acid on the basis of preferential expression characteristics of the codon in a projected host microorganism, e.g., *E. coli*. Other preferred forms of manufactured genes include those wherein: (1) a base codon specifying additional amino acid in the polypeptide synthesized which facilitates direct expression in *E. coli* organisms (e.g., an initial Met residue) and/or (2) base codons specifying urogastrone are preceded and/or followed by a sequence of bases comprising a portion of a base sequence which provides for restriction endonuclease cleavage of a DNA sequence (e.g., a BclI or BamHI site) and consequently facilitates formation of expression vectors.

Also provided by the present invention are: (1) a manufactured gene capable of directing the synthesis in a selected host microorganism of a urogastrone polypeptide analogs which differ from urogastrone in terms of the identity and/or location of one or more amino acids (e.g., [Asp$^{25}$] urogastrone and [Pro$^{52}$, Pro$^{53}$] urogastrone); and (2) a fusion gene comprising a manufactured gene according to the invention fused to a second gene capable of directing synthesis of a second polypeptide (e.g., β-lactamase and β-galactosidase) in a manner permitting the synthesis of a fused polypeptide including urogastrone polypeptide or a urogastrone analog.

In practice of the invention to generate polypeptide products, DNA sequences including manufactured genes are inserted into a viral or circular plasmid DNA vector to form a hybrid vector and the hybrid vectors are employed to transform host microorganisms such as bacteria (e.g., *E. coli*) or yeast cells. The transformed microorganisms are thereafter grown under appropriate nutrient conditions and express the polypeptide products of the invention.

Novel DNA sequences of the invention are preferably synthesized from nucleotide bases according to the methods disclosed in the aforementioned coowned, concurrently-filed U.S. patent application Ser. No. 375,493, by Yitzhak Stabinsky, entitled "Manufacture and Expression of Structural Genes". Briefly summarized, the general method comprises the steps of:

(1) preparing two or more different, linear, duplex DNA strands, each duplex strand including a double stranded region of 12 or more selected complementary base pairs and further including a top single stranded terminal sequence of from 3 to 7 selected bases at one end of the strand and/or a bottom single stranded terminal sequence of from 3 to 7 selected bases at the other end of the strand, each single stranded terminal sequence of each duplex DNA strand comprising the entire base complement of at most one single stranded terminal sequence of any other duplex DNA strand prepared; and (2) annealing each duplex DNA strand prepared in step (1) to one or two different duplex strands prepared in step (1) having a complementary single stranded terminal sequence, thereby to form a single continuous double stranded DNA sequence which has a duplex region of at least 27 selected base pairs including at least three base pairs formed by complementary association of single stranded terminal sequences of duplex DNA strands prepared in step (1) and which has from 0 to 2 single stranded top or bottom terminal regions of from 3 to 7 bases.

In the preferred general process of manufacture, at least three different duplex DNA strands are prepared in step (1) and all strands so prepared are annealed concurrently in a single annealing reaction mixture to form a single continuous double stranded DNA sequence which has a duplex region of at least 42 selected base pairs including at least two nonadjacent sets of 3 or more base pairs formed by complementary association of single stranded terminal sequences of duplex strands prepared in step (1).

The duplex DNA strand preparation step (1) of the DNA sequence manufacturing process noted above preferably comprises the steps of:

(a) constructing first and second linear deoxyoligonucleotide segments having 15 or more bases in a selected linear sequence, the linear sequence of bases of the second segment comprising the total complement of the sequence of bases of the first segment except that at least one end of the second segment shall either include an additional linear sequence of from 3 to 7 selected bases beyond those fully complementing the first segment, or shall lack a linear sequence of from 3 to 7 bases complementary to a terminal sequence of the first segment, provided, however, that the second segment shall not have an additional sequence of bases or be lacking a sequence of bases at both of its ends; and, (b) combining the first and second segments under conditions conducive to complementary association between segments to form a linear, duplex DNA strand.

The sequence of bases in the double stranded DNA subunit sequences formed preferably includes one or more triplet codons selected from among alternative codons specifying the same amino acid on the basis of preferential expression characteristics of the codon in a projected host microorganism, such as yeast cells or bacteria, especially *E. coli* bacteria.

Other aspects and advantages of the present invention will be apparent upon consideration of the following detailed description thereof.

DETAILED DESCRIPTION

As employed herein, the term "manufactured" as applied to a DNA sequence or gene shall designate a product either totally chemically synthesized by assembly of nucleotide bases or derived from the biological replication of a product thus chemically synthesized. As such, the term is exclusive of products "synthesized" by cDNA methods or genomic cloning methodologies which involve starting materials which are initially of biological origin.

The following abbreviations shall be employed herein to designate amino acids: Alanine, Ala; Arginine, Arg; Asparagine, Asn; Aspartic acid, Asp; Cysteine, Cys; Glutamine, Gln; Glutamic acid, Glu; Glycine, Gly; Histidine, His; Isoleucine, Ile; Leucine, Leu; Lysine, Lys; Methionine, Met; Phenylalanine, Phe; Proline, Pro; Serine, Ser; Threonine, Thr; Tryptophan, Trp; Tyrosine, Tyr; Valine, Val. The following abbreviations shall be employed for nucleotide bases: A for adenine; G for guanine; T for thymine; U for uracil; and C for cytosine.

For ease of understanding of the present invention, Table I below provides a tabular correlation between the 64 alternate triplet nucleotide base codons of DNA and the 20 amino acids and transcription termination ("stop") function specified thereby.

TABLE I

| FIRST POSITION | SECOND POSITION | | | | THIRD POSITION |
|---|---|---|---|---|---|
| | T | C | A | G | |
| T | Phe | Ser | Tyr | Cys | T |
| | Phe | Ser | Tyr | Cys | C |
| | Leu | Ser | Stop | Stop | A |
| | Leu | Ser | Stop | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val | Ala | Glu | Gly | G |

The following example illustrastes a preferred general procedure for preparation of deoxyoligonucleotides for use in the manufacture of DNA sequences of the invention.

EXAMPLE 1

Oligonucleotide fragments were synthesized using a four-step procedure and several intermediate washes. Polymer bound dimethoxytrityl protected nucleoside in a sintered glass funnel was first stripped of its 5'-protecting group (dimethoxytrityl) using 3% trichloroacetic acid in dichloromethane for 1½ minutes. The polymer was then washed with methanol, tetrahydrofuran and acetonitrile. The washed polymer was then rinsed with dry acetonitrile, placed under argon and then treated in the condensation step as follows. 0.5 ml of a solution of 10 mg tetrazole in acetonitile was added to the reaction vessel containing polymer. Then 0.5 ml of 30 mg protected nucleoside phosphoramidite in acetonitrile was added. This reaction was agitated and allowed to react for 2 minutes. The reactants were then removed by suction and the polymer rinsed with acetonitrile. This was followed by the oxidation step wherein 1 ml of a solution containing 0.1 molar $I_2$ in 2-6-lutidine/$H_2O$/THF, 1:2:2, was reacted with the polymer bound oligonucleotide chain for 2 minutes. Following a THF rinse capping was done using a solution of dimethylaminopyridine (6.5 g in 100 ml THF) and acetic anhydride in the proportion 4:1 for 2 minutes. This was followed by a methanol rinse and a THF rinse. Then the cycle began again with a trichloroacetic acid in CH$_2$Cl$_2$ treatment. The cycle was repeated until the desired oligonucleotide sequence was obtained.

The final oligonucleotide chain was treated with thiophenol dioxane, triethylamine 1:2:2, for 45 minutes at room temperature. Then, after rinsing with dioxane, methanol and diethylether, the oligonucleotide was cleaved from the polymer with concentrated ammonia at room temperature. After decanting the solution from the polymer, the concentrated ammonia solution was heated at 60° C. for 16 hours in a sealed tube.

Each oligonucleotide solution was then extracted four times with 1-butanol. The solution was loaded into a 20% polyacrylamide 7 molar urea electrophoresis gel and, after running, the appropriate product band was isolated.

The following example illustrates the preparation of a DNA sequence which comprises a gene coding for [Met$^{-1}$] urogastrone and which includes terminal base sequences facilitative of insertion of the sequence into DNA plasmid restriction sites.

EXAMPLE 2

The following deoxyoligonucleotides were synthesized according to the procedures of Example 1.
1. 5'-GG TGG AAC TG CGT TAA TAG-
2. 5'-CAG TAC CGT GAT CTG AAA T
3. 5'-GT TAC ATC GGT GAA CGT TGC
4. 5'-GCT TGC AAC TGC GTA GTT G
5. 5'-GTA ACC AAC TAC GCA GTT G
6. 5'-TACTG GCA ACG TTC ACC GAT
7. 5'-CCA CCA TTT CAG ATC ACGG
8. 5'-GATC CTA TTA ACG CAG TTC
9. 5'-G TAT ATC GAA GCT CTG GAC AAA TAC
10. 5'-AT TGT CTG CAC GAC GGT GTT TGC AT
11. 5'-AA TGC CCG CTG TCC CAC GAC GGT T
12. 5'-G ATC ACA ATC AAC TCT GAT TCC G
13. 5'-GCA TTC GGA ATC AGA GTT CAT TGT
14. 5'-ACA ATA ACC TGC GTG GGA CAG CGG
15. 5'-AT ATA CAT GCA AAC ACC GTC GTG CAG
16. 5'-CA AGC GTA TTT GCA GAG CTT C G The oligonucleotide sequences purified by polyacrylamide gel electrophoresis were phosphorylated at the 5' ends using ATP and T$_4$ polynucleotide kinase in a standard reaction using one nanomole of DNA, a two fold excess of ATP and 1 unit of T$_4$ kinase in 20 μl of buffer made with 5mM hydroxyethylpiperazine ethane sulfonic acid, 10mM MgCl$_2$, 10mM dithiothreitol, pH 7.6. After reaction, the kinase was destroyed by boiling for 5 minutes. These phosphorylated oligonucleotides in the buffer were then used directly for ligation. These sequences are shown in Table 1.

The oligonucleotides in 20 μl standard buffer were combined to form sort duplexes. Each duplex was formed by combining two complementary sequences in equimolar amounts, boiling the mixture, then slow cooling over a ½ hour period to room temperature. In this way, the duplexes in Table II were formed.

TABLE II

```
                                  (12)
              G  ATC  ACA  ATG  AAC  TCT  GAT  TCC  G
                 TGT  TAC  TTG  AGA  CTA  AGG  CTT  ACG
                                  (13)

(11)
         AA  TGC  CCG  CTG  TCC  CAC  GAC  GGT  T
             GGC  GAC  AGG  GTG  ATG  CCA  ATA  ACA
                                  (14)

(10)
         AT  TGT  CTG  CAC  GAC  GGT  GTT  TGC  AT
             GAC  GTG  CTG  CCA  CAA  ACG  TAC  ATA  TA
                                  (15)

(9)
         G  TAT  ATC  GAA  GCT  CTG  GAC  AAA  TAC
            G    CTT  CGA  GAC  CTG  TTT  ATG  CGA  AC
                                  (16)

(4)
               GCT  TGC  AAC  TGC  GTA  GTT  G
                G  TTG  ACG  CAT  CAA  CCA  ATG
                                   (5)

(3)
               GT  TAC  ATC  GGT  GAA  CGT  TGC
                   TAG  CCA  CTT  GCA  ACG  GTC  AT
                                   (6)

(2)
              CAG  TAC  CGT  GAT  CTG  AAA  T
               G   GCA  CTA  GAC  TTT  ACC  ACC
                                   (7)
```

TABLE II-continued

```
                          (1)
      GG  TGG  GAA  CTG  CGT  TAA  TAG
          CTT  GAC  GCA  ATT  ATC  CTA  G
                                    (8)
```

These 8 duplexes were combined sequentially, annealing each set of duplexes at 37° C. for 5 minutes until the final structural gene was in a single tube ready for ligation. The oligonucleotide mixture was then made 150 μmolar in ATP and treated with 84 units of T₄DNA ligase for 16 hours at 4° C. The fully ligated structural gene was then purified by polyacrylamide gel electrophoresis. The final structural gene with appropriate restriction sites is shown in Table III. This was a 175 base pair duplex having Bcl I restriction site at the amino terminal end and a Bam HI site at the carboxy terminal end.

ever, because both restriction sites are destroyed by insertion of the gene in the incorrect orientation, only those clones which contained the gene in the correct orientation were excisable with BclI and BamHI. Those clones with the gene in the correct orientation were characterized by polyacrylamide gel electrophoresis to verify the estimated molecular weight for the urogastrone structural gene.

To further characterize the cloned synthetic DNA segment, the 175 base pair fragment was excised from the chimeric pBR325 plasmid (pHEGF1) and inserted into single-strand bacteriophage M13mp8 relicative

TABLE III

```
        -1   1    2    3    4    5    6    7    8    9
 Bcl I     - Met- Asn- Ser- Asp- Ser- Glu- Cys- Pro- Leu- Ser -
G ATC  ACA  ATG  AAC  TCT  GAT  TCC  GAA  TGC  CCG  CTG  TCC—
       TGT  TAC  TTG  AGA  CTA  AGG  CTT  ACG  GGC  GAC  AGG—

10    11    12    13    14    15    16    17    18    19    20    21
  His - Asp - Gly - Tyr - Cys - Leu - His - Asp - Gly - Val - Cys - Met -
  CAC   GAC   GGT   TAT   TGT   CTG   CAC   GAC   GGT   GTT   TGC   ATG—
  GTG   CTG   CCA   ATA   ACA   GAC   GTC   CTG   CCA   ACC   ACG   TAC—

22    23    24    25    26    27    28    29    30    31    32    33
  Tyr - Ile - Glu - Ala - Leu - Asp - Lys - Tyr - Ala - Cys - Asn - Cys -
  TAT   ATC   GAA   GCT   CTG   GAC   AAA   TAC   GCT   TGC   AAC   TGC—
  ATA   TAG   CTT   AGC   GAC   CTG   TTT   ATG   CGA   ACG   TTG   ACG—

34    35    36    37    38    39    40    41    42    43    44    45
  Val - Val - Gly - Tyr - Ile - Gly - Glu - Arg - Cys - Gln - Try - Arg -
  GTA   GTT   GGT   TAC   ATC   GGT   GAA   CGT   TGC   CAG   TAC   CGT—
  CAT   CAA   CCA   ATG   TAG   CCA   CTT   GCA   ACG   GTC   ATG   GCA—

46    47    48    49    50    51    52    53
  Asp - Leu - Lys - Trp - Trp - Glu - Leu - Arg - Stop  Stop -
  GAT   CTG   AAA   TGG   TGG   GAA   CTG   CGT   TAA   TAG—
  CTA   GAC   TTT   ACC   ACC   CTT   GAC   GCA   ATT   ATC  CTA  G—
                                                                Bam HI
```

Mutant genes coding for polypeptide sequences diferent from the natural sequences were also prepared.

This was done by changing selected segments and repeating the ligation step to obtain the new genes. By altering segments 9 and 16, alanine at residue was changed to aspartic acid. The codon modification was from GCT to GAT. This changes a neutral amino acid residue to an acidic residue and may produce a peptitde with novel characteristics. Another mutant gene was prepared by changing codons in segments 1 and, 8. Specifically, codons for the Leu$^{52}$-Arg$^{53}$ residues (5'- CTG CGT-3') were replaced by those coding for Pro$^{52}$, Pro$^{53}$ (5'-CCG CCA-3'). This gene should code for a peptide resistant to enzyme degradation, but still retaining its other desirable properties.

The following example relates to cloning of the [Met$^{-1}$] urogastrone gene prepared in Example 2.

EXAMPLE 3

The 175 base pair HEGF-URO synthetic gene was inserted into the *E. coli* cloning vector pBR325 using the restriction endonuclease sites BclI and BamHI. Because the restriction sites have the same cohesive termini, the gene was insertable in both orientations. Howform DNA at its BamHI site. Clones with the inserted DNA in a defined orientation were isolated and characterized by polyacrylamide gel eletrophoresis. Single-strand phage for one orientation were isolated and the DNA sequence for the urogastrone structural gene has been determined using the Sanger Dideoxy sequencing technique.

Restriction endonuclease BclI cleaves plasmid pHEGF1 at its unique BclI site lying 7 nucleotides 5' to the translation initiation codon of the urogastrone gene. Approximately 750 nucleotides 5' to this restriction site is a unique restriction endonuclease EcoRI site. Cleavage of pHEGF1 with EcoRI and BclI permitted the insertion of a λ $P_R$ promoter under control of lac repressor between these restriction sites by in vitro recombination to create pHEGF5. Cloning the λ $P_R$ promoter using this approach insured correct orientation of the λ $P_R$-lac promoter-operator relative to the urogastrone structural gene. The λ $P_R$ promoter under lac control used for this construction was an 84 base pair EcoRI BamHI excisable synthetically derived DNA segment in *E. coli* cloning vector pBR322. The BamHI restriction site of the promoter lies one nucleotide 3' to the Shine-Dalgarno sequence. Consequently, fusion of the λ $P_R$ lac promoter with the urogastrone structural gene at their BamHI - BclI cohesive termini junction creates a ribosome binding site with eight nucleotides between the Shine-Dalgarno sequence and the HEGF-URO translation initiation codon. This is close to optimal relative positioning for these two elements. The insertion of the λ $P_R$ promoter in the correct orientation has been verified by restriction enzyme analysis and molecular weight sizing using polyacrylamide gel electrophoresis.

The λ $P_R$-lac-HEGF 259 base pair segment was excised from pHEGF5 using EcoRl and BamHl restriction endonuclease digestion. This fragment was inserted into EcoRl-BamHl digested pBR322 to construct pHEGF10. This construction was performed because pBR322-expressed proteins are more easily analyzed in a maxicell system than pBR325-expressed proteins. In addition, pBR322 is a higher copy number plasmid than pBR325, consequently urogastrone should be expressed in greater amounts in pBR322. The insertion of the λ $P_R$-lac-HEGF DNA segment has been verified by restriction enzyme analysis and polyacrylamide gel electrophoresis.

*E. coli* containing pHEGF5 and pHEGF10 are being examined for expression of urogastrone polypeptide products using the maxicell system. Polypeptide products can be characterized using immunoprecipitation and/or radioimmunoassay techniques with rabbit IgG to mouse EGF.

The following example illustrates the preparation of a DNA sequence which comprises a gene coding for [Met$^{-1}$] urogastrone and which includes terminal base sequences facilitative of insertion of the sequence into DNA plasmid restriction sites as well as internal base sequences facilitative of disassembly and reconstruction of selected portions of the gene.

EXAMPLE 4

The following deoxyoligonucleotides were synthesized according to the general procedures of Example 1.
1. GATCCAA ATG AAC TCT GAT TCC GAA T
2. GC CCG CTG TCT CAT GAC GGT TAC T
3. GC CTG CAT GAT GGC GTA TGC ATG TA
4. C ATC GAA GCT CTG GAC AAA TAC GCA
5. TGC AAC TGT GTT GTA GGT TAC ATC G
6. GC GAA CGT TGC CAG TAT CGC GAC CT
7. G AAA TGG TGG GAA CTG.CGT TAA TAG
8. GG GCA TTC GGA ATC AGA GTT CAT TTG
9. CAG GCA GTA ACC GTC ATG AGA CAG C
10. C GAT GTA CAT GCA TAC GCC ATC ATG
11. TT GCA TGC GTA TTT GTC CAG AGC TT
12. TTC GCC GAT GTA ACC TAC AAC ACA G
13. A TTT CAG GTC GCG ATA CTG GCA ACG
14. TCGA CTA TTA ACG CAG TTC CCA CC The oligonucleotides were combined to form duplexes and sequentially annealed as in Example 2 to yield the structural gene set out in Table IV, having bases forming the "sticky end" of a BamHI restriction site (prior to the polypeptide coding region) and a SalI site (following the transcription termination codons). While the codon usage generally involved selection based on projected use of an *E.coli* bacterial expression system, the codons employed in this gene also resulted in generation of internal recognition sites for cleavage by, e.g., HinfI (5'-GATTC-3'), SphI (5'-GCATGC-3') and NruI (5'-TCGCGA-5').

TABLE IV

| BamHI | -1<br>Met | 1<br>Asn | 2<br>Ser | 3<br>Asp | 4<br>Ser | 5<br>Glu |
|---|---|---|---|---|---|---|
| GATCCAA<br>GTT | ATG<br>TAC | AAC<br>TTG | TCT<br>AGA | G\|AT<br>CTA | TCC<br>A\|GG | GAA<br>CTT |

———— 8 ————
Hinf I

| | 6<br>Cys | 7<br>Pro | 8<br>Leu | 9<br>Ser | 10<br>His | 11<br>Asp | 12<br>Gly |
|---|---|---|---|---|---|---|---|
| | TGC<br>ACG | CCG<br>GGC | CTG<br>GAC | TCT<br>AGA | CAT<br>GTA | GAC<br>CTG | GGT<br>CCA |

———— 2 ————
———— 9 ————

| 13<br>Tyr | 14<br>Cys | 15<br>Leu | 16<br>His | 17<br>Asp | 18<br>Gly | 19<br>Val |
|---|---|---|---|---|---|---|
| TAC<br>ATG | TGC<br>ACG | CTG<br>GAC | CAT<br>GTA | GAT<br>CTA | GGC<br>CCG | GTA<br>CAT |

———— 3 ————
———— 10 ————

| 20<br>Cys | 21<br>Met | 22<br>Tyr | 23<br>Ile | 24<br>Glu | 25<br>Ala | 26<br>Leu |
|---|---|---|---|---|---|---|
| TGC<br>ACG | ATG<br>TAC | TAC<br>ATG | ATC<br>TAG | GAA<br>CTT | GCT<br>CGA | CTG<br>GAC |

———— 4 ————

| 27<br>Asp | 28<br>Lys | 29<br>Tyr | 30<br>Ala | 31<br>Cys | 32<br>Asn | 33<br>Cys |
|---|---|---|---|---|---|---|
| GAC<br>CTG | AAA<br>TTT | TAC<br>ATG | GCA<br>C\|GT | TG\|C<br>ACG | AAC<br>TTG | TGT<br>ACA |

— 11 ————
Sph I

| 34<br>Val | 35<br>Val | 36<br>Gly | 37<br>Tyr | 38<br>Ile | 39<br>Gly | 40<br>Glu | 41<br>Arg |
|---|---|---|---|---|---|---|---|
| GTT<br>CAA | GTA<br>CAT | GGT<br>CCA | TAC<br>ATG | ATC<br>TAG | GGC<br>CCG | GAA<br>CTT | CGT<br>GCA |

— 5 ——
———— 12 ————

| 42<br>Cys | 43<br>Gln | 44<br>Tyr | 45<br>Arg | 46<br>Asp | 47<br>Leu | 48<br>Lys | 49<br>Trp |
|---|---|---|---|---|---|---|---|
| TCG<br>ACG | CAG<br>GTC | TAT<br>ATA | CGC<br>GCG | GAC<br>C\|TG | CTG<br>GAC | AAA<br>TTT | TGG<br>ACC |

— 5 ——
———— 13 ————
Nru I

| 50<br>Trp | 51<br>Glu | 52<br>Leu | 53<br>Arg | Stp | Stp | Sal I |
|---|---|---|---|---|---|---|
| TGG<br>ACC | GAA<br>CTT | CTG<br>GAC | CGT<br>GCA | TAA<br>ATT | TAG<br>ATC | AGCT |

— 7 ——
———— 14 ————

The assembled sequence of Table IV was amplified by insertion into a BamHI/SalI cleaved M13 mp9 vector and then ligated to an EcoRI/BamHI DNA "linker" constructed with an internal XbaI recognition site, as set out in Table V.

TABLE V

| EcoRI | XbaI | | BamHI |
|---|---|---|---|
| GAA TTC T|CT AGA ATG AAG AAA TAT TG | |
| | AGA TC|T TAC TTC TTT ATA ACC TAG | |

Thus provided with an adenosine-rich series of bases prior to the urogastrone polypeptide-specifying sequences, the construction was excised from an amplification plasmid with XbaI and SalI and inserted into a pBR322-derived plasmid (pINT-γ-TXb4) at a manufactured XbaI site following the trp promoter/regulator DNA sequence. The resulting vector, designated pADH25, was employed as an expression vector in a *E. coli* host to generate a polypeptide including a "pro" sequence of 8 amino acids, as set out below, prior to urogastrone polypeptide:

$-8\ -7\ -6\ -5\ -4\ -3\ -2\ -1$
NH$_2$—Met—Lys—Lys—Tyr—Trp—Ile—Gln—Met—[Urogastrone].

The microbially expressed polypeptide displayed the biological activity of naturally-occurring human urogastrone. The levels of expression of the product as determined by bioassay procedures discussed infra were on the order of fifteen micrograms per O.D. liter.

The following example relates to presently preferred procedures for enhancing the levels of expression of products of the invention.

EXAMPLE 5

Plasmid pADH25 was treated with EcoRI and SalI to isolate the entire urogastrone protein coding region (including the DNA sequence coding for the eight residue "pro" sequence) and the entire trp promoter/regulator DNA sequence. The EcoRI/SalI fragment was inserted in a DNA vector containing a temperature sensitive mutation in the copy control region. After transformation with the vector, the host cells normally contain a low copy number of the vector when grown at temperatures of less than 34° C. The plasmid copy number increases 50-fold (i.e., "runs away") within the host cell upon elevation of culture temperature above 34° C. Growth at 37° C. or above will ordinarily be lethal to the transformed host cells.

The new plasmid containing the above-noted EcoRI/SalI insert from pADH25 was designated pADH59. The plasmid was employed to transform *E. coli* K-12 JM103 cells (Bethesda Research Labs.) and samples of the strain harboring pADH59 have been deposited under contract with the American Type Culture Collection, Rockville Md. as A.T.C.C. 393335.

The level of expression of urogastrone analog product by A.T.C.C 393335 was on the order of fifty milligrams per O.D. liter as determined by SDS-PAGE.

The following example relates to a bioassay employed to assess the levels of microbial expression of polypeptides of the present invention.

EXAMPLE 6

A radioreceptor bioassay was developed to assay for biological activity of microbially-expressed products of the invention and was generally patterned on the procedures of Fabricant, et al., *P.N.A.S. U.S.A.*, 74, pp. 565-569 (1977). Briefly put, the assay is a competitive receptor binding assay wherein the amount of urogastrone activity in an unknown sample is determined by the ability to displace radiolabelled urogastrone from bound association with cells in culture. More specifically, cells of human epidermoid carcinoma. cell line A-431 are grown in culture and incubated with fixed quantites of I$^{125}$-labeled urogastrone (Collaborative Research, Boston, Mass.) which binds to specific URO-EGF receptors on the cell surface. The cells are washed to remove excess, unbound labelled materials. Microbial cells transformed for production of urogastrone and urogastrone analog products of the invention are lysed and centrifuged and the supernatant is applied to the culture of A-431 cells and incubated. The culture medium is then assayed for the presence of I$^{125}$-labelled urogastrone displaced from bound association with cell surface receptors by products of the invention present in the microbial cell lysate supernatant.

Polypeptide products of the invention which include amino terminal residues in addition to the native urogastrone sequence may be processed, if desired, to remove the additional residues. For example, the above-noted [Met$^{-1}$]urogastrone may be suitably treated with cyanogen bromide to yield polypeptides commencing with an amino terminal asparagine residue characteristic of the naturally occurring urogastrone products. If such procedures are to be employed, it may be expected that the [Met$^{21}$] residue of urogastrone polypeptide products might provide an additional site for cyanogen bromide cleavage or the methionine may be chemically transformed to a homoserine residue. Alternately, the methionine residue at position 21 may be replaced by another amino acid, such as valine, through reconstruction of the DNA sequence to delete the methioninespecifying codon, ATG, and replace it with an alternate codon, such as GTA which specifies valine. Applied, e.g., to the construction of Example 4, this process would involve an initial variation in construction of oligonucleotide segments 3 and 10. Alternately, the modification could be effected by excising the HinfI/SphI fragment from plasmid pADH59 and replacing it with a manufactured sequence including the desired codon change. The cyanogen bromide cleavage product of microbial expression of such an altered gene would itself be an analog of urogastrone, e.g., [Val$^{121}$]urogastrone.

Products of the present invention and/or antibodies thereto may be suitably "tagged", for example radiolabelled (e.g., with I$^{125}$) conjugated with enzymes or fluorescently labelled, to provide reagent materials useful in assays and/or diagnostic test kits, for the qualitative and/or quantitative determination of the presence of such products and/or said antibodies in fluid samples. Such antibodies may be obtained from the innoculation of one or more animal species (e.g., mice rabbit, goat, human, etc.) or from monoclonal antibody sources. Any of such reagent materials may be used alone or in combination with a suitable substrate, e.g., coated on a glass or plastic particle or bead.

Numerous modifications and variations in the practice of the invention are expected to occur to those skilled in the art upon consideration of the foregoing illustrative examples. Consequently, the invention should be considered as limited only to the extent reflected by the appended claims.

What is claimed is:

1. A non-naturally-occurring polypeptide analog of urogastrone characterized by the presence of one or more of the following alterations in the amino acid sequence of naturally-occurring urogastrone:
    (a) Ala$^{25}$ to Asp$^{25}$;

(b) Leu$^{52}$ to Pro$^{52}$;
(c) Arg$^{53}$ to Pro$^{53}$;
(d) Met$^{21}$ to Val$^{21}$;
(e) addition of Met$^{-1}$; and
(f) addition of all or part of the sequence NH$_2$-Met$^{-8}$-Lys$^{-7}$-Lys$^{-6}$-Tyr$^{-5}$-Trp$^{-4}$-Ile$^{-3}$-Gln$^{-2}$-Met$^{-1}$.

2. A polypeptide analog according to claim 1 selected from the group consisting of:

(a) [Asp$^{25}$]EGF;
(b) [Pro$^{52}$]EGF;
(c) [Pro$^{53}$]EGF;
(d) [Pro$^{52}$Pro$^{53}$]EGF;
(e) [Val$^{21}$]EGF;
(f) and [Met$^{-1}$]forms thereof; and
(g) [Met$^{-8}$Lys$^{-7}$Lys$^{-6}$Tyr$^{-5}$Trp$^{-4}$Ile$^{-3}$Gln$^{-2}$Met$^{-1}$]EGF 7

* * * * *